United States Patent
Yu et al.

(10) Patent No.: US 10,619,148 B2
(45) Date of Patent: Apr. 14, 2020

(54) IMMOBILIZED CELL AND PREPARATION METHOD THEREOF

(71) Applicants: Cathay Biotech Inc., Shanghai (CN); CIBT America Inc., Newark, DE (US)

(72) Inventors: Lijun Yu, Shanghai (CN); Naiqiang Li, Shanghai (CN); Charlie Liu, Shanghai (CN); Xiucai Liu, Shanghai (CN)

(73) Assignees: Cathay Biotech Inc., Shanghai (CN); CIBT America Inc., Newark, DE (US)

( * ) Notice: Subject to any disclaimer, the term of this patent is extended or adjusted under 35 U.S.C. 154(b) by 124 days.

(21) Appl. No.: 15/548,585

(22) PCT Filed: Feb. 3, 2015

(86) PCT No.: PCT/CN2015/072158
§ 371 (c)(1),
(2) Date: Aug. 3, 2017

(87) PCT Pub. No.: WO2016/123745
PCT Pub. Date: Aug. 11, 2016

(65) Prior Publication Data
US 2018/0002686 A1    Jan. 4, 2018

(51) Int. Cl.
| C12N 11/08 | (2020.01) |
| C12N 11/04 | (2006.01) |
| C12N 11/02 | (2006.01) |
| C12N 9/88 | (2006.01) |
| C12R 1/01 | (2006.01) |
| C12P 13/00 | (2006.01) |

(52) U.S. Cl.
CPC ............... *C12N 11/08* (2013.01); *C12N 9/88* (2013.01); *C12N 11/02* (2013.01); *C12N 11/04* (2013.01); *C12P 13/001* (2013.01); *C12Y 401/01018* (2013.01); *C12R 1/01* (2013.01)

(58) Field of Classification Search
CPC ......... C12N 11/08; C12N 11/04; C12N 11/02; C12Y 401/01018
See application file for complete search history.

(56) References Cited

U.S. PATENT DOCUMENTS

2011/0039313 A1    2/2011   Verseck et al.

FOREIGN PATENT DOCUMENTS

| CN | 101240258 A | 8/2008 |
| CN | 101578256 A | 11/2009 |
| CN | 101979534 A | 2/2011 |
| CN | 102056889 A | 5/2011 |
| CN | 102260664 A | 11/2011 |
| CN | 102352387 A | 2/2012 |
| CN | 102782146 A | 11/2012 |
| EP | 1482055 B1 | 3/2006 |
| JP | S62138193 A | 6/1987 |
| JP | 62190080 A | 8/1987 |
| JP | 63024886 A | 2/1988 |
| JP | H01137975 A | 5/1989 |
| JP | 03258398 A | 11/1991 |
| JP | 05168481 A | 7/1993 |
| JP | 06007182 A | 1/1994 |
| JP | 2001302840 A | 10/2001 |
| JP | 2002223770 A | 8/2002 |
| JP | 2002223771 A | 8/2002 |
| JP | 2004000114 A | 1/2004 |
| JP | 2004298033 A | 10/2004 |
| JP | 2005006650 A | 1/2005 |
| JP | 2005060447 A | 3/2005 |
| JP | 2008104453 A | 5/2008 |
| JP | 2008540809 A | 11/2008 |
| JP | 2010517519 A | 5/2010 |

OTHER PUBLICATIONS

Klein & Kressdorf, Methods in Enzymology, vol. 135, 1987, p. 252-259.*
Qian et al. English machine translation of CN 101979534, published on Feb. 23, 2011, 8 pages of PDF.*
Li-Li et al., "Producing Cadaverine by Cell Immobilization of Lysine Decarboxylase," Fine Chemicals (Nov. 2007); 24(11):1079-1084.
Tabor et al., "Construction of an *Escherichia coli* Strain Unable to Synthesize Putresceine, Spermidine, or Cadaverine Characterization of Two Genes Controlling Lysine Decarboxylase," Journal of Bacteriology (Dec. 1980); 144(30):952-956.
Mimitsuka et al., Metabolic Engineering of Corynebacterium glutamicum for Cadaverine Fermentation, Biosci. Biotechnol. Biochem, (2007); 71(9):2130-2135.
Qian et al., "Metabolic Engineering of *Escherichia coli* for the Production of Cadaverine: A Five Carbon Diamine," Biotechnology and Bioengineering (Jan. 1, 2011); 108(1):93-103.

* cited by examiner

*Primary Examiner* — Kade Ariani

(74) *Attorney, Agent, or Firm* — Fox Rothschild LLP

(57) ABSTRACT

Provided are a lysine decarboxylase immobilized cell and preparation method thereof.

16 Claims, No Drawings

IMMOBILIZED CELL AND PREPARATION METHOD THEREOF

FIELD OF THE INVENTION

The present invention relates to an immobilized cell and a method of producing the same, in particular, an immobilized cell containing lysine decarboxylase and a method of producing the same.

BACKGROUND OF THE INVENTION 1,5-pentanediamine (also known as 1,5-pentamethylenediamine, abbreviated as diaminopentane) is an important five-carbon compound in the chemical industry, and is mainly used to produce polyamides, polyurethanes and the like. Additionally, it is also used to produce isocyanates, pyridine, piperidine and other important chemical raw materials.

To date, diamines are chemically produced from petroleum-based starting materials via dicarboxylic acid intermediates or by chemical decarboxylation of amino acids (Albrecht, Klaus, et al., Plastics (5$^{th}$ edition), Winnacker-Kuechler, 2005). Due to the limitations of fossil raw materials and increasing attention on green and environmental protection, it becomes ideal to synthesize diamines through bioengineering processes by utilizing renewable raw materials.

There are two main methods for synthesizing pentanediamine by biological processes. One is to obtain pentanediamine by converting glucose through complex metabolic regulation with microbes, that is, to produce pentanediamine from lysine-producing microorganisms by introducing an optional gene encoding lysine decarboxylase, as described in the following reference document (Tabor, Herbert, et al.; Journal of bacteriology, 144 (3), 952-956, 1980). In 2007, Takashi et al. reported that overexpression of lysine decarboxylase by *Corynebacterium glutamicum* having high ability of lysine synthesis resulted in direct production of pentanediamine by the bacteria during the fermentation with a yield of 2.9 g/l. In studies for improving the yield of pentanediamine, researchers attempted to use *Escherichia coli* strains with plasmids which overexpress homologous host lysine decarboxylase (cadA gene) (see Japanese Patent Application No. JP2002223770A, JP2008104453A, etc.). In Chinese Patent Application No. CN200810005332, it is reported that a lysine-producing bacteria, *Corynebacterium glutamicum*, which overexpresses lysine decarboxylase, is used to produce pentanediamine by fermentation with a yield of about 3.4 g/L in the culture broth. In summary, although the process of producing pentanediamine via direct fermentation of glucose with microbes is simple, it has a long fermentation cycle and the bacteria therein have a limited tolerance to intracellular pentanediamine, resulting in a lower yield of pentanediamine which is unfavorable for a large—scale industrial production.

In further studies, researchers developed another method for producing pentanediamine, that is, culturing a strain overexpressing lysine decarboxylase, and collecting the obtained lysine decarboxylase as a catalyst to catalyze lysine into pentanediamine (see JP2002-223771A, JP2004-000114A, EP1482055B1, JP2005-060447A, etc.). Another example is the use of *Escherichia coli* bacteria which overexpress cadA gene to catalyze lysine adipate and to control the pH during the reaction to improve the stability of the enzyme as described in Chinese Patent Application No. CN101578256A. In Chinese Patent Application No. CN102056889A, it is reported that lysine carbonate is used as a substrate to produce pentanediamine by catalysis, and the carbon dioxide released during the reaction is recycled to control the pH. As described in Chinese Patent No. CN102782146A, a strain expressing cadA gene is subjected to disruption treatment to catalyze exogenous lysine to produce pentanediamine, so as to increase the yield of pentanediamine.

In the above applications or patents, in the process of catalyzing lysine by lysine decarboxylase to produce pentanediamine, a free lysine decarboxylase or cells containing lysine decarboxylase are generally used. Japanese Patent Application No. 2004298033A describes that carrageenan is used to embed lysine decarboxylase-containing strains and then the strains are fermented to produce the enzyme, and then purified lysine salts are catalyzed by the cultured immobilized cells to produce pentanediamine, with about 30% molar conversion of lysine hydrochloride (246 g/L of lysine hydrochloride was catalyzed by the immobilized cells for 150 hours to give pentanediamine at a concentration of 40 g/l).

It is reported that 3 wt % ca-alginate is used to immobilize cells containing lysine decarboxylase, resulting in a poor stability for the immobilized cell. In particular, the enzyme activity in the second time decreased significantly, and in the forth time, the activity of the enzyme decreased to about 38% of the first time (Jiang Lili et al., "Producing Cadaverine by Cell immobilization of Lysine Decarboxylase", Fine Chemicals, 2007, 24 (11), 1080-1084).

In the actual processes, natural polymer gels such as sodium alginate and the like present problems such as a lower strength, being easy to be decomposed by microorganisms, being deformed, disrupted or dissolved during the transformation process, causing leakage of enzymes or cells, a low re-use efficiency of immobilized enzyme, and others.

Cells having lysine decarboxylase activity can catalyze various forms of lysine solutions, for example, purified lysine, hydrochloride, sulfate, phosphate, adipate and other salts of lysine, and unpurified lysine fermentation broth. However, due to the complex composition of lysine fermentation broth, stability of the cells containing lysine decarboxylase is greatly impacted, easily leading to cell lysis, enzyme loss, and reducing utilization efficiency of lysine decarboxylase. Immobilization of the cells containing lysine decarboxylase in a certain carrier will significantly improve the stability of the cells containing lysine decarboxylase in the lysine fermentation broth, improve the catalytic efficiency of the enzyme, and reduce lysine purification costs.

In summary, there are a number of studies on the production of pentanediamine by catalyzing lysine using lysine decarboxylase produced by microorganisms, which are characterized by most use of purified lysine or lysine salt, the need for lysine purification, complex process, and high production costs, and thus limiting the industrial production of pentanediamine. In addition, the reaction system for production of pentanediamine by enzymatic catalysis of lysine mostly uses free enzyme-containing cells, which have low enzyme stability, leading to complex extraction process for pentanediamine in the enzyme reaction solution, affecting the purity of the finished product of pentanediamine, and being not conducive to industrial production.

Accordingly, there is a need in the art for a process that is simpler and more economical and can improve the efficiency of re-use of lysine decarboxylase.

SUMMARY OF THE INVENTION

The first aspect of the present invention relates to a method of immobilizing cells containing lysine decarboxylase comprising the steps of:

a) dissolving a first synthetic macromolecule material in an aqueous solution sufficiently;

b) adding cells to be immobilized which contain lysine dacarboxylase into the resulting solution and immobilizing said cells, wherein the first synthetic macromolecule material is any synthetic macromolecule material having a gel-forming ability, and the immobilization is carried out under conditions that do not destroy the viability of said cells containing lysine decarboxylase.

In some embodiments, the resulting solution further comprises one or more of a natural macromolecule material, a second synthetic macromolecule material, or a mixture thereof, wherein the natural macromolecule material and the second synthetic macromolecule material are natural or synthetic macromolecule materials having a gel-forming ability, and the second synthetic macromolecule material is different from the first synthetic macromolecule material.

In some embodiments, the first synthetic macromolecule material, the second synthetic macromolecule material are one or more selected from the group consisting of polyvinyl alcohol, polyethylene glycol, polyacrylonitrile, acetate fibers and diacetate fibers, and in further embodiments, selected from the group consisting of polyvinyl alcohol and polyethylene glycol.

In some embodiments, the natural macromolecule material is one or more selected from the group consisting of sodium alginate, carrageenan, xanthan gum, activated carbon, diatomaceous earth, curdlan, and chitosan, and in further embodiments, the natural macromolecule material is sodium alginate.

In further embodiments, the resulting solution is a mixed solution of polyvinyl alcohol and sodium alginate or a mixed solution of polyvinyl alcohol and polyethylene glycol. In some embodiments, polyvinyl alcohol is added in an amount of 1 to 13 wt %. In further embodiments, polyvinyl alcohol is added in an amount of 6 to 11 wt %. In further embodiments, polyvinyl alcohol is added in an amount of 7 to 9 wt %. In one embodiment, polyvinyl alcohol is added in an amount of 8 wt %. In some embodiments, sodium alginate is added in an amount of 0.1 to 3 wt %, such as 0.5 to 2.5 wt %, or 1 to 2.0 wt %. In one embodiment, sodium alginate is added in an amount of 1.5 wt %. In some embodiments, ethylene glycol is added in an amount of 0.1 to 5 wt %, such as 0.2 to 3 wt %, 0.3 to 1.5 wt %, or 0.4 to 1 wt %. In one embodiment, polyethylene glycol is added in an amount of 0.5 wt %.

In some embodiments, the immobilization in step b) is carried out by physical immobilization or chemical immobilization, preferably chemical immobilization, more preferably calcium chloride and boric acid crosslinking immobilization, preferably with the calcium chloride solution at a concentration of 0.2 to 5 wt %, such as 0.3 to 3 wt %, 0.4% to 2 wt %, or 0.6 to 1.5 wt %, and in one embodiment with a calcium chloride solution at a concentration of 1 wt %, and with the boric acid solution at a concentration of 1 to 10 wt %, such as 2 to 8 wt %, or 3 to 6 wt %, and in one embodiment with the boric acid solution at a concentration of 4 wt %.

In some embodiments, the method further comprises a step of treating the solution with an epichlorohydrin solution and/or a liquid epoxy resin after the gelation of the solution, preferably adding the epichlorohydrin solution and/or the liquid epoxy resin in an amount of 1 to 1.5 times the theoretical number of moles of hydroxyl groups in PVA and reacting for 20-60 min with oscillation, separating and then washing the particles to obtain the finished product.

In some embodiments, the cells containing lysine decarboxylase are derived from a plant, a microorganism, an insect, or an animal.

In some embodiments, the microorganism is selected from the group consisting of *Bacillus halodurans, Bacillus subtilis, Escherichia coli, Streptomyces coelicolor, Streptomyces pilosus, Eikenella corrodens, Eubacterium acidaminophilum, Salmonella typhimurium, Hafnia alvei, Thermoplasma acidophilum, Pyrococcus abyssi* and *Corynebacterium glutamicum*, preferably selected from the group consisting of *Escherichia coli* and *Hafnia alvei*.

The second aspect of the present invention relates to an immobilized cell containing lysine decarboxylase obtained by the method of immobilizing cells containing lysine decarboxylase according to the first aspect.

The third aspect of the present invention relates to a method of preparing 1,5-pentanediamine comprising steps of contacting the immobilized cell containing lysine decarboxylase according to the second aspect with a liquid containing lysine and obtaining 1,5-pentanediamine.

In some embodiments, the liquid containing lysine is a lysine fermentation broth, a concentrated or diluted solution of a lysine fermentation broth, a degerming lysine fermentation broth after removing bacteria from the lysine fermentation broth and a concentrated or diluted solution of the degerming lysine fermentation broth, and a formulated lysine solution; preferably an original lysine fermentation broth.

In some embodiments, the lysine fermentation broth is obtained by microbial fermentation.

In some embodiments, the microorganism for preparing the lysine fermentation broth is selected from the group consisting of *Corynebacterium* and *Escherichia*, preferably selected from the group consisting of *Escherichia coli* and *Corynebacterium glutamicum*.

In some embodiments, the carbon source for preparing the lysine fermentation broth is a fermentable saccharide; preferably, the fermentable saccharide is derived from a starchy substance, preferably corn or cassava, or a lignocellulosic substance, preferably straw or woods; and more preferably the fermentable saccharide is selected from the group consisting of glucose, fructose and sucrose.

In some embodiments, the liquid containing lysine further comprises a sulfate ion at a concentration equal to or above 0.005 mol/kg.

In some embodiments, the liquid containing lysine further comprises a sugar and a free $NH_4^+$ ion, with a total sugar content equal to or above 300 ppm and a free $NH_4^+$ content equal to or above 0.028 mol/kg.

In some embodiments, the liquid containing lysine is further supplemented with one or more coenzymes selected from the group consisting of pyridoxal, pyridoxal phosphate, pyridoxine and pyridoxamine, preferably pyridoxal 5'-phosphate; preferably, the amount of the coenzymes supplemented is from 0.01 to 0.3 mmol/kg based on the weight of the reaction system.

In some embodiments, the liquid containing lysine contacted with the immobilized cell containing lysine decarboxylase has a pH value of 4.0 to 9.0, preferably 4.5 to 8.5.

In some embodiments, the immobilized cell containing lysine decarboxylase is contacted with the liquid containing lysine at a temperature of 25-55° C., more preferably 28° C. to 45° C.

In some embodiments, the lysine content in the liquid containing lysine is from 1% to 50% (w/w), more preferably from 5% to 20% (w/w).

In other words, a technical problem to be solved by the present invention is to provide an immobilized cell which can be used to produce pentanediamine with a low production cost and a simple process in industrial production and a method of preparing the same, and further to provide a method of producing pentanediamine by using the immobilized cell.

The method of the present invention utilizes a synthetic macromolecule material to immobilize cells containing lysine decarboxylase, to obtain an immobilized cell containing lysine decarboxylase, resulting in significantly improved stability of the enzyme and simplified reaction system and the separation process of pentanediamine. Compared with the previously reported preparation method of pentanediamine by using an immobilized cell, the claimed method can directly use lysine fermentation broth to prepare pentanediamine, improving the catalytic stability of lysine decarboxylase in the lysine fermentation broth having a complex composition, overcoming shortcomings such as high cost, complex process and others caused by the use of pure lysine, lysine hydrochloride, lysine sulfate, lysine carbonate and lysine dicarboxylate as a substrate in the prior art, and reducing the steps for purifying the lysine fermentation broth. Accordingly, the present invention improves the utilization efficiency of the enzyme, simplifies the process for the extraction and production of pentanediamine, saves the lysine purification cost and reduces the cost for the production of pentamethylamine.

DETAILED DESCRIPTION

The present invention is based on the inventors' discovery that after the cells containing lysine decarboxylase immobilized by a synthetic macromolecule material are added to a lysine fermentation broth, a mixed solution containing pentanediamine is obtained. It has been reported in the prior art the preparation of immobilized cells containing lysine decarboxylase using a natural macromolecule material such as sodium alginate and the like. Although the prepared immobilized cells have a high recovery for the enzyme activity, the immobilized cells have an unstable structure and are easy to be collapsed in the course of their use, resulting in decreased utilization stability. Meanwhile, the natural macromolecule material is expensive, which greatly limits its industrial applications. Compared with the utilization of a natural macromolecule material as a carrier, the utilization of a synthetic macromolecule material may improve the structural stability of the immobilized cells and also significantly reduce the cost for preparation of the immobilized cells. However, as of now, synthetic polymeric materials have not been used in the immobilization of the cells containing lysine decarboxylase in practice. This may be because the product of lysine decarboxylase catalyzed reaction, pentanediamine, is a strong polar product, and will be adsorbed to a synthetic polymeric material having a large number of hydroxyl groups, affecting the application of the synthetic polymeric material in the immobilization of the cells having a lysine decarboxylase activity. Accordingly, in some embodiments of the present invention, a synthetic polymeric material and a natural polymeric material are combined as a carrier for the immobilization of the cells containing lysine decarboxylase, thereby combining the advantages of the synthetic polymeric material and the natural polymeric material. The immobilized cells prepared by using these two materials have a better permeability and a more stable structure. In some embodiments of the present invention, the treatments with epichlorohydrin and/or liquid epoxy resin are further introduced to eliminate the mutual adsorption of the polar groups on the commonly used macromolecule material with pentanediamine, significantly increasing the catalytic efficiency of the immobilized cells.

The present invention provides a method of immobilizing cells containing lysine decarboxylase.

The above-mentioned cells containing lysine decarboxylase (abbreviated as LDC, EC4.1.1.18) are cells capable of converting lysine into 1,5-pentanediamine, and the source thereof is not particularly limited and may be derived from any known organism. The lysine decarboxylated cells can be derived from cells of a microorganisms, an animal, a plant or an insect, for example, a wild-type strain, including but not limited to *Bacillus halodurans*, *Bacillus subtilis*, *Escherichia coli*, *Streptomyces coelicolor*, *Streptomyces pilosus*, *Eikenella corrodens*, *Eubacterium acidaminophilum*, *Salmonella typhimurium*, *Hafnia alvei*, *Thermoplasma acidophilum*, *Pyrococcus abyssi* or *Corynebacterium glutamicum*, or the like; the lysine decarboxylase may also be derived from a mutated strain or a genetically engineered bacterium strain of the above-mentioned strain. The lysine decarboxylase may also be a mutant or an active fragment of the lysine decarboxylase from the above-mentioned source, wherein the mutant may be a natural mutant, or a recombinant mutant, and the active fragment may be a truncated protein fragment that retains the lysine decarboxylase activity. The strain or the genetically engineered bacterium comprising the mutant or the active fragment of lysine decarboxylase is also suitable for use in the method of the present invention.

The genetically engineered recombinant cells are not particularly limited and may be, for example, a recombinant cell derived from a microorganism, an animal, a plant or an insect. More specifically, for example, when an animal is used, a mouse, a rat or cultured cells thereof may be given as an example. In addition, when a plant is used, arabidopsis, tobacco or cultured cells thereof, for example, may be given as an example. In addition, when an insect is used, a silkworm or cultured cells thereof, or the like, for example, may be given as an example; and when a microorganism is used, *Escherichia coli*, *Hafnia alvei* or the like, for example, may be given as an example.

The above-mentioned recombinant cells may be used alone or in combination of two or more.

As a method of increasing the activity of lysine decarboxylase in a cell, a method of increasing the amount of the lysine decarboxylase may be employed, for example. Examples of the method of increasing the amount of the enzyme in a cell may include, for example, improvement in the field of gene transcription regulation, increase in gene copy number, improvement of protein translation efficiency, improvement of enzyme catalytic activity, or the like.

Furthermore, the method of culturing the above-mentioned recombinant cells is not particularly limited, and any known method may be used. More specifically, for example, when culturing a microorganism, the culture medium to be used may be a culture medium containing a carbon source, a nitrogen source and an inorganic ion.

The carbon source may be any carbon source used in the art, and examples thereof may include, for example, saccharides such as glucose, lactose, sucrose, galactose, fructose, arabinose, maltose, xylose, trehalose, ribose, a hydrolysate of starch, or the like; alcohols such as glycerol, mannitol, sorbitol, or the like; organic acids such as gluconic acid, fumaric acid, citric acid, succinic acid, or the like. Preferably, glucose, sucrose and starch hydrolyzate are used as a carbon source. The above-mentioned carbon source may be used alone or in combination of two or more.

The nitrogen source may be any nitrogen source used in the art, and examples thereof may include, for example, inorganic ammonium salts such as ammonium sulfate, ammonium chloride, ammonium phosphate, and the like, and organic nitrogen sources such as soybean hydrolyzate, and the like. The above-mentioned nitrogen source may be used alone or in combination of two or more.

The inorganic ion may be any inorganic ion used in the art, and examples thereof may include, for example, sodium ion, magnesium ion, potassium ion, calcium ion, chloride ion, manganese ion, iron ion, phosphate ion, sulfate ion, and the like. One or more of the above inorganic ions may be added to the culture medium.

In addition, additional micronutrients may be added to the culture medium as needed, and examples thereof may include, for example, various amino acids, trace elements and vitamins and the like.

The above-mentioned culture medium may be any culture medium used in the art, and more specifically, examples thereof may include, for example, LB medium, such as LB medium containing 1% peptone, 0.5% yeast powder, and 1% sodium chloride and with a pH value of 7.0.

The culture conditions for the cells containing lysine decarboxylase of the present invention are not particularly limited. For example, when culturing *Hafnia alvei*, under an aerobic condition, the culture temperature may be, for example, in a range of 20 to 45° C., preferably of 25 to 38° C.; the pH value for the culture may be, for example, in a range of 5.0 to 8.5, preferably of 5.5 to 7.5; and the culture time may be, for example, in a range of 10 to 50 hours.

The present invention also provides a method of preparing an immobilized cell comprising the following steps: a) adding 1 to 13 wt % (percent weight) of a first synthetic macromolecule material to the water and dissolving it, for example, by heating and stirring; b) adding to the resulting solution cells containing lysine decarboxylase at 20° C. to 40° C., dissolving it under stirring, and gelling the solution to obtain immobilized cells. The first synthetic macromolecule material may be any synthetic macromolecule material having a gel-forming ability.

In the above-mentioned preparation method, the resulting solution may further comprise one of a natural macromolecule material and a second synthetic macromolecule material, or a mixture thereof. The addition of the natural macromolecule material or the second synthetic macromolecule material is not particularly limited as long as a homogeneous solution can be obtained, and may be performed before the addition of the first synthetic macromolecule material or simultaneously with the first synthetic macromolecule material, or after the addition of the first synthetic macromolecule material. In some embodiments, the second synthetic macromolecule material is added to the solution containing the first synthetic macromolecule material in a ratio of 1:20 to 1:4 of the first synthetic macromolecule material and dissolved under stirring to obtain a homogeneous solution. The natural macromolecule material and the second synthetic macromolecule material may be any natural or synthetic macromolecule materials having a gel-forming ability.

The first synthetic macromolecule material or the second synthetic macromolecule material may be one or more of polyvinyl alcohol, polyethylene glycol, polyacrylonitrile, acetate fibers, polyacrylamide, diacetate fibers and the like, preferably polyvinyl alcohol and polyethylene glycol. The molecular weight of polyethylene glycol used is in a range of from 1000 to 8000 daltons, such as 1000, 1500, 2000, 2500, 3000, 3500, 4000, 4500, 5000, 5500, 6000, 6500, 7000, 7500, 8000 daltons and any molecular weight between them. The specific choice of the second synthetic macromolecule material may be different from that of the first synthetic macromolecule material. When polyvinyl alcohol and polyethylene glycol are selected as the synthetic macromolecule materials, the first synthetic macromolecule material is preferably polyvinyl alcohol, and the second synthetic macromolecule material is preferably polyethylene glycol. In some embodiments, when polyacrylamide and carrageenan are selected as the carriers for immobilization, polyacrylamide is used as the first synthetic polymer and the carrageenan is used as the natural macromolecule material.

The amount of the first synthetic macromolecule material such as polyvinyl alcohol is not particularly limited in the present invention as long as it can be dissolved in water. However, if the concentration is too low, the immobilized material as formed will have a loosened structure and the lysine decarboxylase will be liable to leak out. When the concentration of the first synthetic macromolecule material such as polyvinyl alcohol is less than 0.5 wt %, the immobilized material as formed will be too loose to be suitable for the preparation of immobilized cells. In some embodiments, the first synthetic macromolecule material such as polyvinyl alcohol is added in an amount of from 1 to 13 wt %, preferably from 6 to 11 wt %, of the water.

The method of dissolving the first synthetic macromolecule material such as polyvinyl alcohol is not particularly limited in the present invention. In some embodiments, the water is heated to 50 to 100° C. and the first synthetic polymeric material such as polyvinyl alcohol is added and stirred to be dissolved.

In some embodiments, the natural macromolecule material and/or the second synthetic macromolecule material is added in an amount of from 1/20 to 1/4 of the amount of the first synthetic macromolecule material such as polyvinyl alcohol, more preferably from 1/10 to 1/5 of the amount of the first synthetic macromolecule material such as polyvinyl alcohol. In some embodiments, the polyethylene glycol is added in an amount of from 1/20 to 1/4 of the amount of the first synthetic macromolecule material such as polyvinyl alcohol, more preferably from 1/10 to 1/5 of the amount of the first synthetic macromolecule material such as polyvinyl alcohol.

The natural macromolecule material described in the present invention includes, but is not limited to, sodium alginate, carrageenan, chitosan, agarose, carrageenan, gelatin and the like. In some embodiments, the natural macromolecule material is sodium alginate, and in some embodiments the natural macromolecule material is carrageenan.

In the present invention, the enzyme-containing cell is added in an amount of 0.5 to 7% by weight of the above-mentioned solution based on the cells containing lysine decarboxylase, and a concentrated enzyme fermentation broth containing 10 to 50% of water may be added based on the weight of the above-mentioned solution.

The method for gelling the synthetic macromolecule material is not particularly limited in the present invention, and a boric acid method may be used, or a freezing method may be used. In one embodiment, 1 to 10 wt % of boric acid solution, preferably 3 to 6 wt % of boric acid solution is added to the solution, and the solution of the immobilized cells is dropped into the obtained boric acid solution to form spherical particles. In one embodiment, the solution of the immobilized cells is frozen at −5 to −20° C. for 10 to 40 hours, thawed at room temperature, then dehydrated in a saturated sodium sulfate solution and then granulated. In one embodiment, the solution of the immobilized cells is frozen at −5 to −20° C. for 10 to 40 hours, thawed at room temperature, then dehydrated in a saturated ammonium sulfate solution and then granulated.

The method of preparing an immobilized cell of the present invention further comprises the steps of, after the gelation of the solution, adding an epichlorohydrin solution and/or a liquid epoxy resin in an amount of 1 to 1.5 times the theoretical number of moles of hydroxyl groups in polyvinyl alcohol (PVA) and reacting for 20-60 min with oscillation, separating and then washing the particles to obtain the finished product. In the present invention, the application of just PVA to replace all or a part of sodium alginate as an immobilizing material can only substantially achieve the object of the present invention, the reason for this may be in that PVA carries a large number of hydroxyl groups, while the pentanediamine is a polar substance and thus, will be adsorbed in a large quantity to the PVA; a too high concentration of the pentanediamine will have a strong product inhibition effect on the enzymatic conversion reaction. As such, the efficiency of enzymatic conversion reaction will become low. Treatment with epichlorohydrin and/or liquid epoxy resin may change the surface properties of the carrier and eliminate the adsorption of the carrier to the product. Not only PVA, the carrier surface properties of other synthetic macromolecule materials used in the present invention such as polyethylene glycol, polyacrylonitrile, acetate fibers, diacetate fibers may also be changed by treatment with epichlorohydrin and/or liquid epoxy, to eliminate the adsorption of the carrier to the product. As demonstrated in the examples below, the treatment with epichlorohydrin and/or liquid epoxy resin significantly improved the stability and the application effects of the immobilized cells containing lysine decarboxylase.

The epichlorohydrin of the present invention may be present in a form of an aqueous solution or an alcoholic solution at a concentration of 1 to 5.5 wt %. In some embodiments, the granulated immobilized cells are added into 1 to 5.5 wt % epichlorohydrin solution and reacted at 20 to 50° C., 100 to 300 rounds per minute for 20 to 120 min with oscillation.

The liquid epoxy resin of the present invention selected is an epoxy resin having an epoxy group and being liquid at room temperature. The molecular weight of the epoxy resin is not particularly limited and may be used as long as it is a liquid epoxy resin. Its application amount is specifically determined based on the epoxy group content of the epoxy resin, and in some embodiments, epichlorohydrin may be added in an amount of 1 to 1.5 times the theoretical number of moles of hydroxyl groups in PVA.

The present invention further discloses a method of preparing pentanediamine, comprising the steps of:

A) contacting lysine or a salt thereof with said immobilized cells; and

B) solid-liquid separating to obtain a solution containing pentanediamine.

The lysine or a salt thereof is not particularly limited in the present invention and may be any liquids containing lysine, such as a lysine fermentation broth, a concentrated or diluted solution of a lysine fermentation broth, a degerming lysine fermentation broth after removing bacteria from the lysine fermentation broth and a concentrated or diluted solution of the degerming lysine fermentation broth, a purified or partially purified lysine fermentation broth, or a solution formulated from lysine and a salt thereof; preferably a lysine fermentation broth. The salt of lysine includes, but is not limited to, lysine hydrochloride, lysine sulfate, lysine carbonate, lysine phosphate, lysine adipate, and lysine sebacate.

In some embodiments of the present invention, the immobilized cells are contacted with lysine or a salt thereof at a temperature of 30 to 50° C. and the pH value of the solution containing lysine or a salt thereof is in a range of from 5 to 7.

In some embodiments of the present invention, when the immobilized cells are contacted with lysine or a salt thereof, the lysine or a salt thereof in the solution is at a concentration of 6 to 30 wt %, preferably 8 to 20 wt %.

In some embodiments of the invention, a coenzyme is added when the immobilized cells are contacted with lysine or a salt thereof. The coenzymes may be one or more selected from the group consisting of pyridoxal, pyridoxal phosphate, pyridoxine, and pyridoxamine, and more preferably pyridoxal 5'-phosphate. In some embodiments, the coenzymes are added in an amount of from 0.01 to 0.5 mmol/kg based on the weight of the reaction system (the weight of all reactive materials except for the coenzymes).

After completion of the reaction, a mixed solution containing pentanediamine (i.e., a reaction terminating solution) is obtained, and there is no particular requirement for the solid-liquid separation, for example, centrifugation, filtration and the like. A conventionally known technique may be used. There is no particular requirement for the method of extracting pentanediamine from the supernatant after the solid-liquid separation, for example, the method as described in Japanese Patent Application No. JP200400114A may be used, which involves the following steps: firstly adjusting the pH of the solution to 12 to 14, then extracting with an organic solvent, and distilling the extract liquor under a reduced pressure to give pentanediamine.

The original lysine fermentation broth described in the present application may include all of the lysine fermentation broth produced in the prior art.

In the present invention, the lysine fermentation broth used may comprise an inorganic ion such as $Cl^-$, $SO_4^{2-}$, and the like.

In the present invention, the lysine fermentation broth further comprises various residual components such as residual sugar, residual nitrogen and the like after fermentation in the culture medium.

The method of producing pentanediamine by catalysis of a lysine fermentation broth using the cells expressing lysine decarboxylase immobilized with a synthetic macromolecule material of the present invention has the following advantages: 1) immobilization of the cells containing lysine decarboxylase improves the utilization efficiency of the enzyme, is conducive to simplify the production process of pentanediamine, and improves the quality of the pentanediamine products.

2) The improvement of the stability of the immobilized cells results in that the method can directly use the original lysine fermentation broth to prepare pentanediamine, overcome the shortcomings such as high cost, complex process and others caused by the use of pure lysine, lysine hydrochloride, lysine sulfate, lysine carbonate, lysine dicarboxylate and others as a substrate in the prior art, reduce the steps for purifying the lysine fermentation broth, simplify the process, and reduce the cost for the production of pentamethylamine.

The present invention will now be illustrated by way of the preparation examples below to make the features and advantages of the present invention more clear, but the present invention is not limited to the examples set forth herein. Unless otherwise specified, all the proportions of the components in the culture medium are represented by the weight ratio, the concentration is represented by the mass percentage, and the lysine content is based on the lysine hydrochloride. Unless otherwise specified, the raw materials used in the examples are commercially available.

EXAMPLES

Preparation Example 1: Preparation of Lysine Decarboxylase Fermentation Broth

The lysine decarboxylase fermentation broth was prepared as follows:

(1) Seed Culture

A stock solution of the genetically engineered *Hafnia alvei* bacteria expressing lysine decarboxylase kept in glycerol (Cathay, Shandong, P.R. China) was inoculated into a 500 ml seed vial with 100 ml of liquid culture medium (LB medium, containing 1% peptone, 0.5% yeast powder, and 1% sodium chloride, pH 7.0), and incubated at 30° C., 250 rmp for 30 hours.

(2) Fermentation of Lysine Decarboxylase

In a 5 L fermentor, 3 liters of LB medium was added and sterilized at 121° C. for 20 minutes, then the above seed solution was inoculated for fermentation (The fermentation medium formulation was LB medium: 1% peptone, 0.5% yeast powder, 1% sodium chloride, pH 7.0). The fermentation started at 30° C., 500 rpm, with a controlled ventilation volume of 1 vvm and a tank pressure of 0.1 MPa; an alkaline solution was used to control the pH value to 7.0 during the fermentation, and the fermentation was stopped after fermentation for 30 hours (h). After the fermentation is finished, the enzyme-containing cells were collected by centrifugation for preparing immobilized cells.

Comparative Example 1: Preparation of Immobilized Cells Containing Lysine Decarboxylase Using Carrageenan (1) Preparation of Immobilized Cells 100 ml of water was boiled, added with 4 g of carrageenan, stirred and heated until the carrageenan was dissolved sufficiently, and then cooled to room temperature. Then, 1 g of cells containing lysine decarboxylase prepared in Preparation Example 1 was added and the solution was homogenized by sufficiently stirring. The solution was dripped into 2-5% CaCl$_2$ aqueous solution with a needle to generate particles with a diameter of about 3 to 8 mm. The immobilized cells were collected by filtration for future use.

(2) Catalysis of Lysine Fermentation Broth with Immobilized Cells

The immobilized cells were loaded into a reaction column having a height-diameter ratio of 3:1, and a commercially available lysine fermentation broth having a lysine content of 20% was diluted to a concentration of 8%, and a coenzyme was added to a final concentration of 0.1 mM. The lysine fermentation broth containing the coenzyme was passed through the column from the bottom of the enzyme reaction column, the flow rate was adjusted to ensure that the residual amount of lysine in the effluent was less than 0.1% (W/W) and the reaction temperature was controlled at 40° C. The yield of pentanediamine, the utilization time of immobilized cells and the morphological changes of immobilized cells were shown in Table 1.

Comparative Example 2: Preparation of Immobilized Cells Containing Lysine Decarboxylase Using Sodium Alginate (1) Preparation of Immobilized Cells 100 ml of water was boiled, added with 3-5 g of sodium alginate, stirred and heated until the sodium alginate was dissolved sufficiently, and then cooled to room temperature. Then, 1 g of cells containing lysine decarboxylase obtained in Preparation Example 1 was added and the solution was homogenized by sufficiently stirring. The solution was dripped into 2-5% CaCl$_2$ aqueous solution with a needle to generate particles with a diameter of about 3 to 8 mm. The immobilized cells were collected by filtration for future use.

(2) Catalysis of Lysine Fermentation Broth with Immobilized Cells

The immobilized cells were loaded into a reaction column having a height-diameter ratio of 3:1, and a lysine fermentation broth having a concentration of 8% was passed through the immobilized cell column, the flow rate was adjusted to ensure that the residual amount of lysine in the effluent was less than 0.1% (W/W) and the reaction temperature was controlled at 40° C. The reaction solution was continually collected and concentrated and then distilled to obtain a pentanediamine product. The yield of pentanediamine, the utilization time of immobilized cells and the morphological changes of immobilized cells were shown in Table 1.

Comparative Example 3: Catalytic Efficiency of Free Cells Containing Lysine Decarboxylase for Lysine Fermentation Broth 1 g of cells containing lysine decarboxylase was added to 10 g of lysine fermentation broth having a concentration of 8% in a triangular flask. A coenzyme was added to a final concentration of 0.1 mM. The reaction was catalyzed at 40° C., 200 rpm for 1 h, with lysine conversion of 99.25%. The cells were collected by centrifugation to catalyze the lysine fermentation broth repeatedly. After a total of 3 hours of reaction, a part of the enzyme-containing cells were disrupted. The amount of the cells recovered by centrifugation was only 0.5 g, the catalytic efficiency for the lysine fermentation broth was decreased to below 40%, and the relative enzyme activity was significantly decreased. The results were shown in Table 1.

Example 1: Preparation of Immobilized Cells Containing Lysine Decarboxylase Using Polyvinyl Alcohol (1) Preparation of Immobilized Cells 100 ml of water was boiled, added with 8 g of polyvinyl alcohol, stirred and further heated until the polyvinyl alcohol was dissolved sufficiently, and cooled to room temperature. Then, 3 g of bacterial suspension containing the cells containing lysine decarboxylase obtained in Preparation Example 1 was added and the solution was homogenized by sufficiently stirring, frozen to solidification in a refrigerator at −20° C., removed from the refrigerator, added with saturated sodium sulfate to remove 80% of the water, and cut into particles with a diameter of about 4-8 mm.

(2) Catalysis of Lysine Fermentation Broth with Immobilized Cells

The immobilized cells were loaded into a reaction column having a height-diameter ratio of 3:1, and a fermentation broth containing 8% lysine was passed through the immobilized cell column. The flow rate was adjusted to ensure that the residual amount of lysine in the effluent was less than 0.1% (W/W) and the reaction temperature was controlled at 40° C. The enzymatically decarboxylated solution was collected, concentrated and distilled to obtain a finished pentanediamine product.

The yield of pentanediamine, the utilization time of immobilized cells and the morphological changes of immobilized cells were shown in Table 1.

Example 2: Preparation of Immobilized Cells Containing Lysine Decarboxylase Using a Mixture of Polyvinyl Alcohol and Sodium Alginate (1) Preparation of Immobilized Cells 7 g of polyvinyl alcohol was added to 100 ml of water, and the mixture was heated and stirred until the polyvinyl alcohol was sufficiently dissolved. Then, 1.5 g of sodium alginate was added and heated to be dissolved uniformly. After cooled to room temperature, a certain amount of wet cells containing lysine decarboxylase was added. The solution was stirred sufficiently and added dropwise to a solution of 6% boric acid to form particles. The particles of the immobilized cells were collected after washing with water 3 times.

(2) Catalysis of Lysine Fermentation Broth with Immobilized Cells

The immobilized cells were loaded into a reaction column having a height-diameter ratio of 3:1, and a fermentation broth containing 8% lysine was passed through from the bottom of the column. The flow rate was adjusted to ensure that the residual amount of lysine in the effluent was less than 0.1% (W/W) and the reaction temperature was controlled at 40° C. The reaction solution was collected, concentrated and distilled to obtain a finished pentanediamine product.

The yield of pentanediamine, the utilization time of immobilized cells, the morphological changes of immobilized cells, and the relative residual enzyme activity of immobilized cells were shown in Table 1.

Example 3: Preparation of Immobilized Cells Containing Lysine Decarboxylase Using a Mixture of Polyvinyl Alcohol and Polyethylene Glycol (1) Preparation of Immobilized Cells 7 g of polyvinyl alcohol was added to 100 ml of water, and the mixture was heated and stirred until the polyvinyl alcohol was sufficiently dissolved. Then, 0.5 g of polyethylene glycol (PEG5000) was added and heated to be dissolved uniformly. After cooled to room temperature, 1.5 g of cells containing lysine decarboxylase was added. The solution was stirred sufficiently, oven-dried and shaped, and cut into particles. The particles were washed and collected to obtain the immobilized cells.

(2) Catalysis of Lysine Fermentation Broth with Immobilized Cells

The immobilized cells were loaded into a reaction column having a height-diameter ratio of 3:1, and a fermentation broth containing 8% lysine was passed through from the bottom of the column. The flow rate was adjusted to ensure that the residual amount of lysine in the effluent was less than 0.1% (W/W) and the reaction temperature was controlled at 40° C. The reaction solution was concentrated and distilled to obtain a finished pentanediamine product.

The yield of pentanediamine, the utilization time of immobilized cells, the morphological changes of immobilized cells, and the relative residual enzyme activity of immobilized cells were shown in Table 1.

Example 4: Treatment of Immobilized Cells with Epichlorohydrin (1) Preparation of Immobilized Cells 100 ml of water was added with 7 g of polyvinyl alcohol, heated and stirred until the polyvinyl alcohol was dissolved sufficiently. Then, 1.5 g of sodium alginate was added and heated to be dissolved uniformly. After cooled to room temperature, 2 g of cells containing lysine decarboxylase was added and the mixture was stirred well. To the solution a 4% boric acid solution containing 1% calcium chloride was added dropwise to form spherical particles. The particles were removed out and washed three times with water and then added to a 5% epichlorohydrin alcoholic solution. After shaking at 200 rpm for 2 hours at room temperature, the mixture was washed with water to remove epichlorohydrin, and the immobilized cells were collected.

(2) Catalysis of Lysine Fermentation Broth with Immobilized Cells

The immobilized cells were loaded into a reaction column having a height-diameter ratio of 3:1, and a lysine fermentation broth having a concentration of 8% (w/v) was passed through from the bottom of the column. The flow rate was adjusted to ensure that the residual amount of lysine in the effluent was less than 0.1% (W/W) and the reaction temperature was controlled at 40° C. The reaction solution was concentrated and distilled to obtain a finished pentanediamine product.

The yield of pentanediamine, the utilization time of immobilized cells, the morphological changes of immobilized cells, and the relative residual enzyme activity of immobilized cells were shown in Table 1.

Example 5: Epichlorohydrin Treatment of Immobilized Cells (1) Preparation of Immobilized Cells 100 ml of water was added with 8 g of polyvinyl alcohol, heated and stirred until the polyvinyl alcohol was dissolved sufficiently. After cooled to room temperature, 2 g of cells containing lysine decarboxylase was added and the mixture was stirred sufficiently. To the solution a 4% boric acid solution containing 1% calcium chloride was added dropwise to form spherical particles. The particles were removed out and washed three times with water and then added to a 5% epichlorohydrin alcoholic solution. After shaking at 200 rpm for 2 hours at room temperature, the mixture was washed with water to remove epichlorohydrin, and the immobilized cells were collected.

(2) Catalysis of Lysine Fermentation Broth with Immobilized Cells

The immobilized cells were loaded into a reaction column having a height-diameter ratio of 3:1, and a lysine fermentation broth having a concentration of 8% (w/v) was passed through from the bottom of the column. The flow rate was adjusted to ensure that the residual amount of lysine in the effluent was less than 0.1% (W/W) and the reaction temperature was controlled at 40° C. The reaction solution was concentrated and distilled to obtain a finished pentanediamine product.

The yield of pentanediamine, the utilization time of immobilized cells, the morphological changes of immobilized cells, and the relative residual enzyme activity of immobilized cells were shown in Table 1.

TABLE 1

| Examples | Carrier for Immobilization | Yield of Pentanediamine | Utilization Time | Morphological Changes of Immobilized Cells | Relative Residual Enzyme Activity (%) |
|---|---|---|---|---|---|
| Comparative Example 1 | carrageenan | 99.23 | continuous use for 15 h | particles of immobilized cells were disrupted, cells were leaked with loss, not suitable for continuous use. | 30% |
| Comparative Example 2 | sodium alginate | 99.90% | continuous use for 18 h | particles of immobilized cells were disrupted, cells were leaked with loss, not suitable for continuous use. | 42% |
| Comparative Example 3 | free cells | 99.25% | continuous use for 6 h | cells were disrupted, protein was lost, not suitable for continuous use. | 30% |
| Example 1 | polyvinyl alcohol | 99.89% | continuous use for 48 h | particles of immobilized cells kept intact, suitable for continuous use. | 70% |
| Example 2 | polyvinyl alcohol and sodium alginate | 99.68% | continuous use for 64 h | particles of immobilized cells kept intact, suitable for continuous use. | 78% |
| Example 3 | polyvinyl alcohol and polyethylene glycol | 99.82% | continuous use for 60 h | particles of immobilized cells were not as good as those of Example 2, decarboxylation rate decreased. | 80% |
| Example 4 | polyvinyl alcohol and sodium alginate, via treatment with epichlorohydrin | 99.65% | continuous use for 120 h | polarity of carrier surface decreased, incapable of absorbing products. particles kept intact, suitable for continuous use | 82% |
| Example 5 | polyvinyl alcohol, via treatment with epichlorohydrin | 99.34% | continuous use for 150 h | Polarity of carrier surface decreased, incapable of absorbing products, particles kept intact, suitable for continuous use | 85% |

Note:
The yield of pentanediamine is the ratio of the mole number of pentylenediamine produced in a certain reaction time to the molar number of the initial lysine in the reaction solution.

Although only the method of catalyzing the differently treated lysine fermentation broths by the immobilized cells containing lysine decarboxylase prepared by the embedding method is described in the Examples of the present invention, those skilled in the art would appreciate that the method of the present invention is not limited thereto and can also be applied to the immobilization of other enzyme-containing cells and other lysine-containing solutions.

We claimed:

1. A method of immobilizing cells containing lysine decarboxylase, consisting of the steps of:
   a) dissolving polyvinyl alcohol, or a mixture of polyvinyl alcohol and sodium alginate, or a mixture of polyvinyl alcohol and polyethylene glycol, in an aqueous solution sufficiently;
   b) adding cells to be immobilized containing lysine decarboxylase into the resulting solution and immobilizing said cells, and
   c) treating the solution with an epichlorohydrin aqueous solution after gelation of the solution thereby immobilizing said cells containing lysine decarboxylase,
   wherein polyvinyl alcohol is added in an amount of 1 to 13 wt %, sodium alginate is added in an amount of 0.1 to 3 wt %, and the polyethylene glycol is added in an amount of 0.1 to 5 wt %, wherein the epichlorohydrin presents in a form of an aqueous solution at a concentration of 1 to 5.5 wt %, and wherein the immobilization is carried out under conditions that do not destroy the viability of said cells containing lysine decarboxylase.

2. The method of immobilizing cells containing lysine decarboxylase according to claim 1, wherein the immobilization in step b) is carried out by physical immobilization or chemical immobilization.

3. The method of immobilizing cells containing lysine decarboxylase according to claim 1, wherein the cells containing lysine decarboxylase are derived from a plant, a microorganism, an insect or an animal.

4. The method of immobilizing cells containing lysine decarboxylase according to claim 3, wherein the microorganism is selected from the group consisting of Bacillus halodurans, Bacillus subtilis, Escherichia coli, Streptomyces coelicolor, Streptomyces pilosus, Eikenella corrodens, Eubacterium acidaminophilum, Salmonella typhimurium, Hafnia alvei, Thermoplasma acidophilum, Pyrococcus abyssi and Corynebacterium glutamicum.

5. An immobilized cell containing lysine decarboxylase obtained by the method of immobilizing cells containing lysine decarboxylase according to claim 1.

6. A method of preparing 1,5-pentanediamine comprising steps of contacting the immobilized cell containing lysine decarboxylase according to claim 5 with a liquid containing lysine and obtaining 1,5-pentanediamine.

7. The method of preparing 1,5-pentanediamine according to claim 6, wherein the liquid containing lysine is a lysine fermentation broth, a concentrated or diluted solution of a lysine fermentation broth, a degerming lysine fermentation broth after removing bacteria from the lysine fermentation broth and a concentrated or diluted solution of the degerming lysine fermentation broth, and a formulated lysine solution.

8. The method of preparing 1,5-pentanediamine according to claim 7, wherein the lysine fermentation broth is obtained by microbial fermentation.

9. The method of preparing 1,5-pentanediamine according to claim 8, wherein the microorganism for preparing the lysine fermentation broth is selected from the group consisting of Corynebacterium and Escherichia.

10. The method of preparing 1,5-pentanediamine according to claim 8, wherein the carbon source for preparing the lysine fermentation broth is a fermentable saccharide.

11. The method of preparing 1,5-pentanediamine according to claim 6, wherein the liquid containing lysine further comprises a sulfate ion at a concentration equal to or above 0.005 mol/kg.

12. The method of preparing 1,5-pentanediamine according to claim 6, wherein the liquid containing lysine further comprises a sugar and a free $NH_4^+$ ion, with a total sugar content equal to or above 300 ppm and a free $NH_4^+$ content equal to or above 0.028 mol/kg.

13. The method of preparing 1,5-pentanediamine according to claim 6, wherein the liquid containing lysine is further supplemented with one or more coenzymes selected from the group consisting of pyridoxal, pyridoxal phosphate, pyridoxine and pyridoxamine, the amount of the coenzymes supplemented is from 0.01 to 0.3 mmol/kg based on the weight of the reaction system.

14. The method of preparing 1,5-pentanediamine according to claim 6, wherein the liquid containing lysine contacted with the immobilized cell containing lysine decarboxylase has a pH value of 4.0 to 9.0.

15. The method of preparing 1,5-pentanediamine according to claim 6, wherein the immobilized cell containing lysine decarboxylase is contacted with the liquid containing lysine at a temperature of 25 to 55° C., more preferably 28° C. to 40° C.

16. The method of preparing 1,5-pentanediamine according to claim 6, wherein the lysine content in the liquid containing lysine is from 1% to 50% (w/w).

* * * * *